United States Patent [19]

Regel et al.

[11] 4,073,636
[45] Feb. 14, 1978

[54] AZOLYLAMIDINE COMPOUNDS AND HERBICIDAL COMPOSITIONS

[75] Inventors: Erik Regel, Wuppertal; Ludwig Eue; Robert R. Schmidt, both of Cologne, all of Germany

[73] Assignee: Bayer Aktiengesellschaft, Leverkusen, Germany

[21] Appl. No.: 607,986

[22] Filed: Aug. 26, 1975

Related U.S. Application Data

[62] Division of Ser. No. 459,156, April 8, 1974, Pat. No. 3,993,469.

[30] Foreign Application Priority Data

Apr. 27, 1973 Germany ............................. 2321330

[51] Int. Cl.$^2$ ...................... A01N 9/22; C07D 231/12
[52] U.S. Cl. ........................................... 71/92; 71/94; 260/293.7; 548/378; 548/374
[58] Field of Search ......................... 260/310 R, 293.7; 71/92, 94

[56] References Cited

U.S. PATENT DOCUMENTS 3,833,605  9/1974  Karadavidoff et al. .......... 260/310 R

OTHER PUBLICATIONS

Davidoff et al. Chemical Abstracts vol. 79, 143852W 1973.

Primary Examiner—Natalie Trousof
Assistant Examiner—Jane T. Fan
Attorney, Agent, or Firm—Burgess, Dinklage & Sprung

[57] ABSTRACT

New azolylamidines of the formula

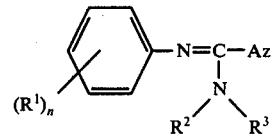

(I)

wherein
  $n$ is an integer from 0 to 5,
  $R^1$ is halogen, alkyl, alkoxy, alkylthio, haloalkoxy, haloalkylthio, halophenoxy or haloalkyl;
  $R^2$ and $R^3$, independently of one another, are each hydrogen, alkyl, alkoxyalkyl, cycloalkyl, alkoxy or alkoxycarbonylalkyl, of, preferably not more than 7 carbon atoms; or taken together, represent a lower alkylene bridge which can be interrupted by one or more hetero-atoms; and
  Az represents an azolyl radical selected from imidazol-1-yl, pyrrol-1-yl, pyrazol-1-yl, 1,2,4-triazol-1-yl, 1,2,4-triazol-4-yl or 1,2,3-triazol-1-yl, and their salts are outstandingly effective herbicides showing particularly selective action.

23 Claims, No Drawings

AZOLYLAMIDINE COMPOUNDS AND HERBICIDAL COMPOSITIONS

This is a divisional application of Ser. No. 459,156, filed Apr. 8, 1974, now U.S. Pat. No. 3,993,469 issued on Nov. 23, 1976.

This invention relates to certain new azolylamidine compounds, to herbicidal compositions containing them, and to their use as herbicides.

It is known, from German Auslegeschrift (German Published Specification) No. 1,089,210 and U.S. Pat. No. 3,399,233 that guanidines, especially 2-phenyl-1,1,3,3-tetramethyl-guanidine, can be used for combating weeds. However, the activity of these compounds is not always entirely satisfactory if low amounts and low concentrations are used.

The present invention provides, as new compounds, azolyl-amidines of the formula

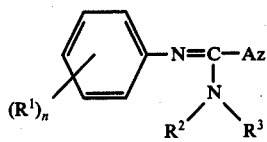

(I)

in which
n is 0, 1, 2, 3, 4 or 5,
$R^1$ is halogen, alkyl, alkoxy, alkylthio, halogenoalkoxy, halogenoalkylthio, halogenophenoxy or halogenoalkyl, the $R^1$ substituents being selected independently of one another when n is greater than 1, preferably $R^1$ contains no more than 6 carbon atoms;
$R^2$ and $R^3$, independently of one another, are each hydrogen, alkyl, alkoxyalkyl, cycloalkyl, alkoxy or alkoxycarbonylalkyl, of, preferably not more than 7 carbon atoms; or, taken together represent a lower alkylene bridge which can be interrupted by one or more hetero-atoms or hetero-groups and which, together with the adjoining nitrogen, forms a three-membered, five-membered or six-membered, heterocyclic ring and
Az represents an azolyl radical selected from imidazol-1-yl, pyrrol-1-yl, pyrazol-1-yl, 1,2,4-triazol-1-yl, 1,2,4-triazol-4-yl or 1,2,3-triazol-1-yl, the said azolyl radicals optionally carrying one or more substituents selected from lower alkyl (of up to 6 carbon atoms) aryl, halogen and nitro and/or optionally containing one or more fused benzene rings.
and their salts with physiologically tolerated acids.

The compounds of this invention have been found to display excellent herbicidal properties.

Surprisingly, the new azolyl-amidines according to the invention and their salts with physiologically tolerated acids show a substantially greater herbicidal potency than the guanidines known from the state of the art, for example 2-phenyl-1,1,3,3-tetramethyl guanidine, which is chemically the nearest active compound. The compounds according to the invention thus represent an enrichment of the art.

Preferably $R^1$ is chlorine, alkyl of from 1 to 4 carbon atoms (for example methyl), alkoxy of from 1 to 3 carbon atoms (for example methoxy), alkylthio of from 1 to 3 carbon atoms (for example methylthio), halogenophenyloxy (especially chlorophenoxy) or halogenoalkoxy, halogenoalkylthio or halogenoalkyl of from, in each case, 1 or 2 carbon atoms and 2 to 5 halogen atoms (especially chlorine and fluorine, as in trifluoromethoxy, pentafluoroethoxy, trifluoromethylthio and difluorochloromethylthio); $R^2$ and $R^3$ are each hydrogen, alkyl or alkoxy of from in either case 1 to 4 (especially 1 to 3) carbon atoms, alkoxyalkyl or alkoxycarbonylalkyl of from, in either case, 1 to 3 carbon atoms in the alkoxy moiety and 1 to 2 carbon atoms in the alkyl moiety, or cycloalkyl of from 3 to 7 carbon atoms, (especially of from 5 to 7 carbon atoms), or $R^2$ and $R^3$ conjointly form an alkylene bride which can be interrupted by one or two hetero-atoms, selected from oxygen and sulfur, or by the hetero-grouping —NH— or —NCH$_3$—, and which forms, with the adjoining nitrogen atom, a three-membered, five-membered or six-membered heterocyclic ring; and Az is one of the radicals

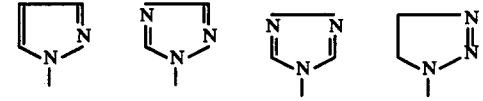

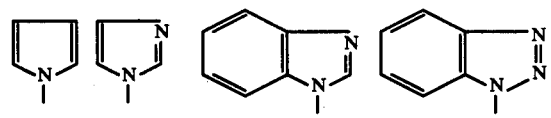

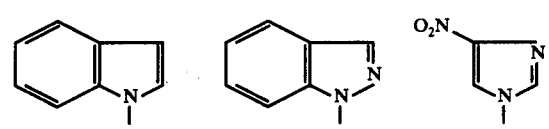

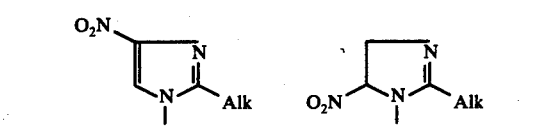

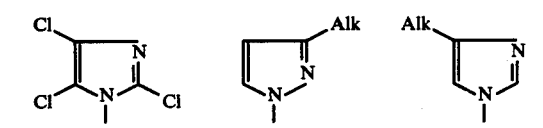

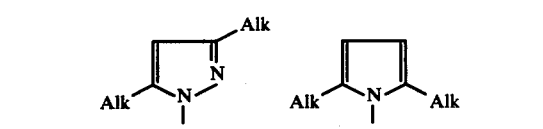

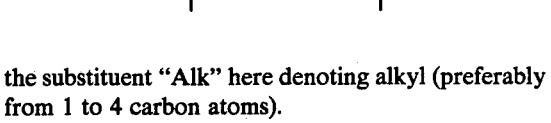

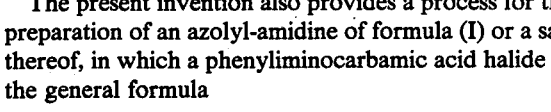

the substituent "Alk" here denoting alkyl (preferably of from 1 to 4 carbon atoms).

The present invention also provides a process for the preparation of an azolyl-amidine of formula (I) or a salt thereof, in which a phenyliminocarbamic acid halide of the general formula

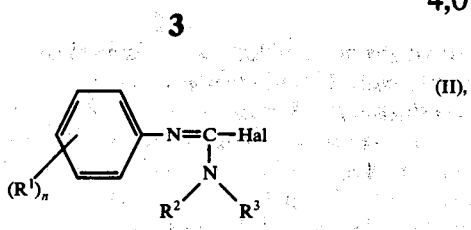

or a hydrogen halide adduct thereof, of the formula

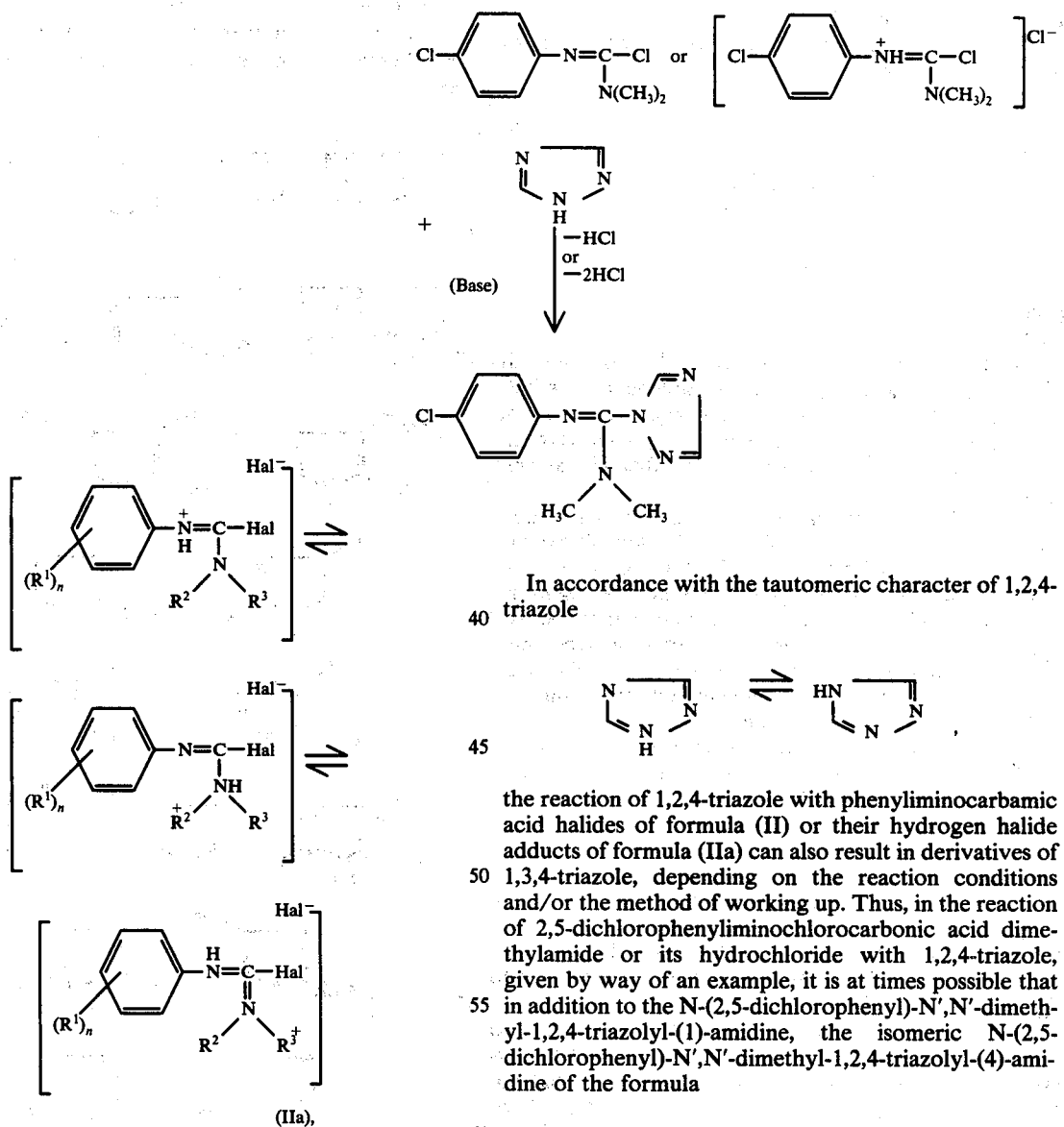

in which
R¹, R², R³ and n have the above-mentioned meanings and
Hal is halogen, especially chlorine,
is reacted with an azole of the formula Az — H  (III), in which
Az has the above-mentioned meaning, in the presence of an acid-binding agent and optionally in the presence of a polar solvent. The azolyl-amidines (I) obtainable according to the invention can be converted into the salts by reaction with acids according to customary methods; conversely the salts of the azolyl-amidines, also obtainable according to the invention, can be converted into the free azolyl-amidines (I) by treatment with bases, according to customary methods.

If 4-chlorophenylimino-chlorocarbonic acid dimethylamide or its hydrochloride and 1,2,4-triazole are used as starting materials, the course of the reaction can be represented by the following equation:

In accordance with the tautomeric character of 1,2,4-triazole the reaction of 1,2,4-triazole with phenyliminocarbamic acid halides of formula (II) or their hydrogen halide adducts of formula (IIa) can also result in derivatives of 1,3,4-triazole, depending on the reaction conditions and/or the method of working up. Thus, in the reaction of 2,5-dichlorophenyliminochlorocarbonic acid dimethylamide or its hydrochloride with 1,2,4-triazole, given by way of an example, it is at times possible that in addition to the N-(2,5-dichlorophenyl)-N',N'-dimethyl-1,2,4-triazolyl-(1)-amidine, the isomeric N-(2,5-dichlorophenyl)-N',N'-dimethyl-1,2,4-triazolyl-(4)-amidine of the formula

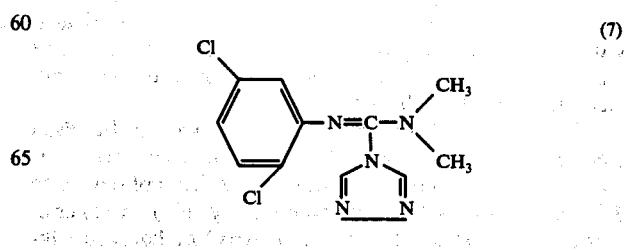

(7)

is also formed; the latter can, however, be isolated (see Example 5 hereinafter).

The carbamic acid halides of formula (II) and their hydrogen halide adducts of formula (IIa), which can be used according to the invention, are in part known (see French Patent Specification No. 1,256,873). The carbamic acid halides of formula (II) which have not previously been described in the literature can be prepared by reacting known isocyanide-dichlorides of the general formula

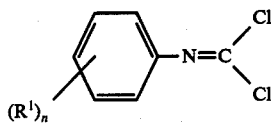
(VI)

in which $R^1$ and $n$ have the above-mentioned meanings with an equimolar amount of an amine of the general formula

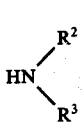
(VII)

in which $R^2$ and $R^3$ have the above-mentioned meaning in accordance with methods known in principle (see German Auslegeschriften (German Published Specifications) No. 1,170,931 and 1,089,210). The hydrogen halide adducts of formula (IIa) which have not previously been described in the literature can be prepared by reacting 1-phenylureas of the general formula

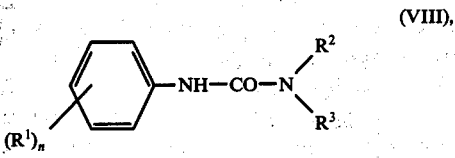
(VIII), in which $R^1$, $R^2$, $R^3$ and $n$ have the above-mentioned meanings, with chlorinating agents, such as phosphorus pentachloride, in a manner known in principle. See German Auslegeschrift (German Published Specification) No. 1,129,161.

The following may be mentioned as examples of the starting compounds of the formula (II) and (IIa); phenylimino-chlorocarbonic acid ethyleneamide, phenylimino-chlorocarbonic acid amide, phenylimino-chlorocarbonic acid dimethylamide, phenylimino-chlorocarbonic acid diethylamide, 4-chlorophenylimino-chlorocarbonic acid dimethylamide, 4-chlorophenylimino-chlorocarbonic acid methylmethoxyamide, 4-chlorophenylimino-chlorocarbonic acid diethylamide, 4-chlorophenylimino-chlorocarbonic acid methylpropylamide, 4-chlorophenylimino-chlorocarbonic acid methylisopropylamide, 4-chlorophenylimino-chlorocarbonic acid methylbutylamide, 3-trifluoromethylphenylimino-chlorocarbonic acid dimethylamide, 4-methylphenylimino-chlorocarbonic acid dimethylamide, 3-methylphenylimino-chlorocarbonic acid dimethylamide, 4-ethylphenylimino-chlorocarbonic acid dimethylamide, 4-butylphenylimino-chlorocarbonic acid dimethylamide, 4-ethoxyphenylimino-chlorocarbonic acid dimethyl-amide, 4-methoxyphenylimino-chlorocarbonic acid dimethylamide, 4-methylthiophenylimino-chlorocarbonic acid dimethylamide, 4-trifluoromethylphenylimino-chlorocarbonic acid dimethylamide, 4-chlorophenylimino-chlorocarbonic acid ethyleneamide, 3,4-dichlorophenylimino-chlorocarbonic acid ethyleneamide, 3,4-dichlorophenylimino-chlorocarbonic acid dimethylamide, 3,4-dichlorophenylimino-chlorocarbonic acid methylmethoxyamide, 2,4-dichlorophenylimino-chlorocarbonic acid dimethylamide, 2,5-dichlorophenylimino-chlorocarbonic acid dimethylamide, 2,6-dichlorophenylimino-chlorocarbonic acid dimethylamide, 2,3-dichlorophenylimino-chlorocarbonic acid dimethylamide, 3-chloro-4-methoxyphenylimino-chlorocarbonic acid dimethylamide, 3-chloro-4-methylthiophenylimino-chlorocarbonic acid dimethylamide, 3-chloro-4-ethylthiophenylimino-chlorocarbonic acid dimethylamide, 3-chloro-4-ethyl-thiophenylimino-chlorocarbonic acid methylbutylamide, 2,3,4-trichlorophenylimino-chlorocarbonic acid dimethylamide, 3,4,5-trichlorophenylimino-chlorocarbonic acid dimethylamide, 2,4,5-trichlorophenylimino-chlorocarbonic acid dimethylamide, 2,4,6-trichlorophenylimino-chlorocarbonic acid dimethylamide, 2,3,6-trichlorophenylimino-chlorocarbonic acid dimethylamide, 1,2,3,4,5-pentachlorophenylimino-chlorocarbonic acid dimethylamide, 4-chloro-2-trifluoromethylphenylimino-chlorocarbonic acid dimethylamide, 3-chloro-4-trifluoromethylphenylimino-chlorocarbonic acid dimethylamide, 4-chloro-3-trifluoromethylphenylimino-chlorocarbonic acid dimethylamide, 4-chloro-2-methylphenylimino-chlorocarbonic acid dimethylamide, 4-chloro-3-methylphenylimino-chlorocarbonic acid dimethylamide, 3-chloro-4-methoxyphenylimino-chlorocarbonic acid dimethylamide, 3-chloro-4-methylphenylimino-chlorocarbonic acid dimethylamide, 3-chloro-4-methylphenylimino-chlorocarbonic acid methylbutylamide, phenylimino-chlorocarbonic acid (ethoxycarbonylmethyl)methylamide, phenylimino-chlorocarbonic acid methylcylcohexylamide, phenylimino-chlorocarbonic acid ethylamide, 4-trifluoromethylphenylimino-chlorocarbonic acid dimethylamide hydrochloride, 2-methyl-4-trifluoromethylphenylimino-chlorocarbonic acid dimethylamide hydrochloride, 3-trifluoromethylphenylimino-chlorocarbonic acid dimethylamide hydrochloride, 4-trifluoromethoxyphenylimino-chlorocarbonic acid dimethylamide hydrochloride, 3-pentafluoroethoxyphenylimino-chlorocarbonic acid dimethylamide hydrochloride, 3-chloro-4-trifluoromethoxyphenylimino-chlorocarbonic acid dimethylamide hydrochloride, 3-chloro-4-methylthiophenylimino-chlorocarbonic acid methylbutylamide, 3-trifluoromethoxyphenylimino-chlorocarbonic acid dimethylamide hydrochloride, 3-chloro-4-chlorodifluoromethylthiophenylimino-chlorocarbonic acid dimethylamide hydrochloride, 3,4-dichlorophenylimino-carbonic acid methylmethoxyamide hydrochloride, 4-chlorophenylimino-chlorocarbonic acid dimethylamide hydrochloride, 3,4-dichlorophenylimino-chlorocarbonic acid methylbutylamide hydrochloride, 3,4-dichlorophenylimino-chlorocarbonic acid morpholide hydrochloride, 3,4-dichlorophenylimino-chlorocarbonic acid piperide hydrochloride, 3,4-dichlorophenylimino-chlorocarbonic acid piperazide hydrochloride, phenylimino-chlorocarbonic acid cyclohexylamide hydrochloride, 3,4-dichlorophenylimino-chlorocarbonic acid 4'-methylpiperazide hydrochloride, phenyliminochlorocarbonic acid pyrolidinylamide hydrochloride and (4-chlorophenoxy)-phenylimino-chlorocarbonic acid dimethylamide hydrochloride.

The following starting materials of formula (III) may be mentioned: pyrrole, pyrazole, 1,2,4-triazole, 1,2,3-triazole, imidazole, 2-methylimidazole, 2-ethylimidazole, 2-propylimidazole, 2-isopropylimidazole, benzotriazole, benzimidazole, indole, 4-methylimidazole, 4-ethylimidazole, 4-nitroimidazole, 2-methyl-4-nitroimidazole, 2-methyl-5-nitroimidazole, 4-methyl-5-nitroimidazole, 2,4-dimethyl-imidazole, 2-methyl-4-ethylimidazole, 2-chloroimidazole, 4,5-dichloroimidazole and 2,4,5-trichloroimidazole.

The azoles of formula (III) used as starting materials are known.

The azolyl-amidines (I) according to the invention can be converted into salts by reaction with acids, preferably with physiologically tolerated acids, according to customary methods. Examples of such physiologically tolerated acids are the hydrogen halide acids, for example hydrobromic acid and, in particular, hydrochloric acid, and also phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as 1,5-naphthalenedisulfonic acid.

Polar organic solvents can be used as diluents for the reaction according to the invention. Preferred solvents include chlorinated hydrocarbons, such as chlorobenzene; ketones, such as acetone or diethyl ketone; nitriles, such as acetonitrile; and ethers, such as tetrahydrofuran and dioxane.

All acid acceptors usually employed can be used as acid binding agents. Preferably, alkali metal hydroxides, alkali metal carbonates and organic bases are used: piperidine, pyridine, triethylamine and sodium carbonate are particularly suitable. Furthermore, an excess of an azole of the formula (III) can also be employed as the acid-binding agent.

The reaction temperatures can be varied within a fairly wide range. In general, the reaction is carried out at between 0° and 80° C, preferably between 20° and 50° C. The reaction is generally carried out under normal pressure.

In carrying out the process according to the invention, 1 to 1.1 moles of azole of formula (III) and 1 to 1.1 moles of acid-binding agent are generally employed per 1 mole of starting material of formula (II). Per mole of starting material of formula (IIa), 1 to 1.5 moles of azole of formula (III) are generally employed, together with either 1 to 1.2 moles of acid-binding agent, if it is desired to obtain a salt (hydrogen halide adduct) of an azolyl-amidine as the end product, or with 2 to 2.5 moles of acid-binding agent, if it is desired to obtain a free azolyl-amidine (I) as the end product.

To isolate the free azolyl-amidines (I), the hydrohalide of the acid-binding agent, which may have been produced, is first filtered off, and the filtrate is freed of the solvent in vacuo. The oil which remains is taken up in an organic solvent and the solution is washed with water until free of salt. The organic phase is dried, the solvent is distilled off and the resulting oil is purified by distillation and, if it crystallizes out, by recrystallization.

To isolate salts of the azolyl-amidines, the hydrohalide of the acid-binding agent, which may have separated out, is again first filtered off. The filtrate is freed of the solvent in vacuo, leaving the azolyl-amidine salt; should this be obtained in an oily form, it can be caused to crystallize by trituration with a suitable solvent, such as ethyl acetate.

The preparation of the compounds of the present invention is illustrated in the following preparative Examples:

EXAMPLE 1

Preparation of N-phenyl-N', N'-dimethyl-imidazolyl-(1)-amidine

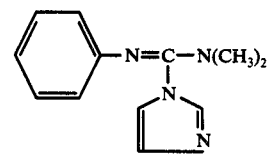

(3)

Variant a 1.095 kg (5 moles) of phenyliminochlorocarbonic acid dimethylamide hydrochloride were suspended in 2 l of acetonitrile. 374 g (5.5 moles) of imidazole were introduced into this suspension with external cooling, during which addition the temperature rose to about 50° C. 1.111 kg (11 moles) of triethylamine were then added dropwise with external cooling and under a reflux condenser.

After stirring for 15 hours at room temperature, the triethylammonium chloride which had separated out was filtered off. The solvent of the filtrate was then distilled off under reduced pressure, the residue was taken up in 2 l of methylene chloride and the solution was washed with water until free of salt. The organic phase was dried over sodium sulfate and freed of the solvent in vacuo and the oily residue was triturated with diisopropyl ether; this caused it to become crystalline.

835 g (78% of theory) of N-phenyl-N', N'-dimethylimidazolyl-(1)-amidine of melting point 70° C were obtained.

Variant b 22 g (0.1 mole) of phenyliminochlorocarbonic acid dimethylamide hydrochloride were introduced into a solution of 6.8 g (0.1 mole) of imidazole in 300 ml of acetonitrile, whilst cooling. 10.1 g (0.1 mole) of triethylamine were added dropwise. After stirring for 15 hours, the triethylammonium chloride which had separated out was filtered off and the filtrate was free of the solvent.

The oil which remained was dissolved in 500 ml of water and a solution of 4 g (0.1 mole) of sodium hydroxide in 100 ml of water was added. The aqueous solution was extracted with ether and the ether solution was dried over anhydrous sodium sulfate, filtered and freed of the solvent.

20.5 g (96% of theory) of N-phenyl-N',N'-dimethylimidazolyl-(1)-amidine of melting point 70° C were obtained.

The starting material could be prepared as follows:

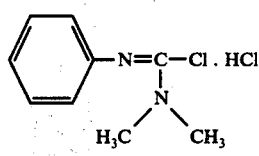

326 g (2 moles) of N-phenyl-N',N'-dimethyl-urea were mixed with 417 g (2moles) of phosphorus pentachloride in a stirring apparatus equipped with a descending condenser, and the mixture was heated to 60°–80° C, until the reaction started. Thereafter, the temperature of the reaction mixture rose, with vigorous evolution of hydrogen chloride, and about one-third of the phosphorus oxychloride formed distilled off.

After the reaction had subsided, the mixture was heated to 100° C for 4 hours whilst stirring and was then cooled to 60° C, and 300 ml of ethyl acetate were added. After stirring for 15 hours, the crystals which had separated out were filtered off at room temperature.

367 g (83.5% of theory) of phenyliminochlorocarbonic acid dimethylamide hydrochloride of melting point 140° C were obtained. A further 28 g were obtained from the filtrate by distilling off the solvent in vacuo and triturating the residue with ethyl acetate.

Total yield: 395 g (90% of theory).

EXAMPLE 2

Preparation of N-4-chlorophenyl-N',N'-dimethylpyrazolyl-(1)-amidine (4)

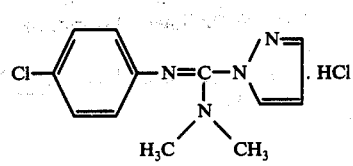

38.1 g (0.15 mole) of 4-phenyliminochlorocarbonic acid dimethylamide hydrochloride were introduced into a solution of 10.2 g (0.15 mole) of pyrazole in 500 ml of acetonitrile and 15.2 g (0.15 mole) of triethylamine were then added dropwise. After stirring for 15 hours at room temperature, the triethylammonium chloride which had separated out was filtered off and the filtrate was freed of the solvent in vacuo.

42 g (98% of theory) of N-4-chlorophenyl-N',N'-dimethyl-pyrazolyl-(1)-amidine hydrochloride of melting point 170° C was obtained.

(2)

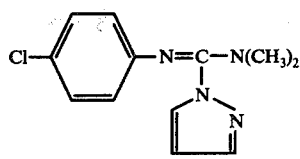

The hydrochloride was dissolved in 500 ml of water, the aqueous solution was filtered and an aqueous solution containing 6 g (0.15 mole) of sodium hydroxide was added. The aqueous solution was extracted with ether and the ether phase was worked up in the usual manner.

34 g (91.5% of theory) of N-4-chlorophenyl-N',N'-dimethyl-pyrazolyl-(1)-amidine of melting point 76° C were obtained.

EXAMPLE 3

Preparation of N-2,4,6-trichlorophenyl-N',N'-dimethyl-1,2,4,-triazolyl-(1)-amidine (5)

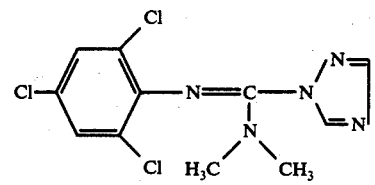

A solution of 3.5 g (0.05 mole) of 1,2,4-triazole and 5.1 g (0.05 mole) of triethylamine in 150 ml of acetonitrile was added dropwise to a solution of 14.3 g (0.05 mole) of 2,4,6-trichlorophenyliminochlorocarbonic acid dimethylamide in 150 ml of acetonitrile at room temperature. After stirring for 15 hours at room temperature, the triethylammonium chloride which had separated out was filtered off and the filtrate is freed of the solvent in vacuo. The residue was dissolved in chloroform and the solution was washed with water until free of salt. The organic phase was dried and filtered and the solvent was distilled off. The resulting oil was caused to crystallize by trituration with diethyl ether. 8.5 g (53% of theory) of N-2,4,6-trichlorophenyl-N',N'-dimethyl-1,2,4-triazolyl-(1)-amidine of melting point 140° C were obtained.

The starting material could be prepared as follows:

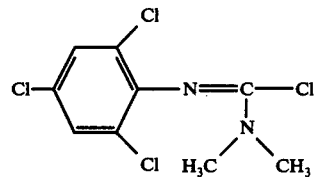

89 g (0.37 mole) of 2,4,6-trichlorophenylisocyanide dichloride were dissolved in 1,000 ml of acetone. Dimethylamine was passed into this solution at 0° C, whilst cooling. After the exothermic reaction had ended, the dimethylammonium chloride which had separated out was filtered off and the solvent of the filtrate was distilled off. After triturating the semicrystalline mass with a little diisopropyl ether and subsequently filtering, 55.6 g (61% of theory) of 2,4,6-trichlorophenylimino-chlorocarbonic acid dimethylamide of melting point 82° C were obtained.

EXAMPLE 4

Preparation of N-(3,4-dichlorophenylimino)-N',N'-dimethyl-pyrazolyl-(1)-amidine hydrochloride (6)

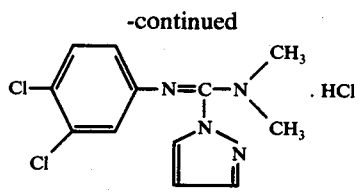

10.2 g (0.15 mole) of pyrazole were dissolved in 300 ml of acetonitrile and 43.5 g (0.15 mole) of 3,4-dichlorophenyliminochlorocarbonic acid dimethylamide hydrochloride were added in portions. After the exothermic reaction had subsided, 15.2 g (0.15 mole) of triethylamine were added dropwise, whilst stirring. After stirring for 15 hours at room temperture, the triethylammonium chloride which had separated out was filtered off, the filtrate was freed of the solvent in vacuo and the oil which remained was triturated with acetone. The residual triethylammonium chloride which had separated out was filtered off. The solvent of the filtrate was again distilled off and the resulting oil was triturated with ethyl acetate.

40 g (83% of theory) of N-(3,4-dichlorophenylimino)-N',N'-dimethyl-pyrazolyl-(1)-amidine hydrochloride of melting point 120° C were obtained.

EXAMPLE 5

Preparation of N-2,5-dichlorophenylimino-N,N'-dimethyl-1,2,4,-triazolyl-(4)-amidine

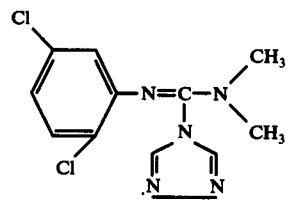

(7)

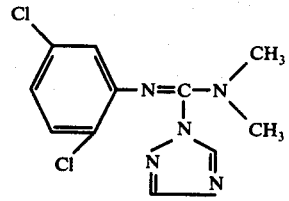

(8)

28.8 g (0.1 mole) of 2,5-dichlorophenyliminocarbonic acid dimethylamide hydrochloride were suspended in 300 ml of acetonitrile and 27.6 g (0.4 mole) of 1,2,4-triazole and 40.4 g (0.4 mole) of triethylamine were added. After standing for 15 hours at room temperature, the triethylammonium chloride which had separated out was filtered off, the filtrate was freed of the solvent in vacuo, the residue was dissolved in ethyl acetate and the solution was washed with water until free of salt. After drying, and distilling off the ethyl acetate, the crystalline mixture was triturated with ether.

12.5 g (44% of theory) of N-2,5-dichlorophenylimino-N,N'-dimethyl-1,2,4-triazolyl-(4)amidine of melting point 165° C were obtained. The nuclear resonance spectrum showed, for the azole protons, a singlet with the intensity of 2-protons at 8.87 ppm ($\delta$ CH$_2$ at 60 MH$_z$, TMS as the internal standard, d-DMSO as the solvent). The ether solution, after distilling off the ether and triturating the residual oil with diisopropyl ether, gave 6 g (2% of theory) of N-2,5-dichlorophenylimino-N',N'-dimethyl-1,2,4-triazolyl-(1)-amidine of melting point 120° C. The nuclear resonance spectrum showed, for the azole protons, two signals each with the intensity of one proton, at 8.2 and 8.78 ppm ($\delta$ CH$_2$ at 60 MH$_z$, TMS as the internal standard, d-DMSO as the solvent).

The compounds listed in Table 1 which follows can be prepared analogously:

Table 1

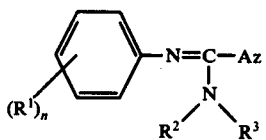

(I)

| Ex. No. | R$^1$ | n | R$^2$ | R$^3$ | Az | Physical characteristics |
|---|---|---|---|---|---|---|
| 6 | 3,4-Cl$_2$ | 2 | CH$_3$ | CH$_3$ | pyrazolyl | m.p. 60° C |
| 7 | — | 0 | CH$_3$ | CH$_3$ | pyrazolyl | n$_D^{20}$ 1.5910 |
| 8 | 3-CF$_3$ | 1 | CH$_3$ | CH$_3$ | pyrazolyl | n$_D^{20}$ 1.5340 |
| 9 | 3-Cl, 4-OCH$_3$ | 2 | CH$_3$ | CH$_3$ | pyrazolyl | m.p. 63° C |

Table 1-continued (I)

$$\text{(R}^1\text{)}_n\text{-C}_6\text{H}_4\text{-N=C(Az)-N(R}^2\text{)(R}^3\text{)}$$

| Ex. No. | R¹ | n | R² | R³ | Az | Physical characteristics |
|---|---|---|---|---|---|---|
| 10 | 3-Cl, 4-CH$_3$ | 2 | CH$_3$ | CH$_3$ | pyrazol-1-yl | m.p. 28° C |
| 11 | 2,5-Cl$_2$ | 2 | CH$_3$ | CH$_3$ | pyrazol-1-yl | $n_D^{20}$ 1.5860 |
| 12 | 2,4-Cl$_2$ | 2 | CH$_3$ | CH$_3$ | pyrazol-1-yl | $n_D^{20}$ 1.5661 |
| 13 | 2,6-Cl$_2$ | 2 | CH$_3$ | CH$_3$ | pyrazol-1-yl | m.p. 102° C |
| 14 | 4-Cl, 2-CH$_3$ | 2 | CH$_3$ | CH$_3$ | pyrazol-1-yl | $n_D^{20}$ 1.5825 |
| 15 | 4-Cl, 2-CF$_3$ | 2 | CH$_3$ | CH$_3$ | pyrazol-1-yl | m.p. 74° C |
| 16 | 3,5-Cl$_2$ | 2 | CH$_3$ | CH$_3$ | pyrazol-1-yl | m.p. 63° C |
| 17 | 2,4,6-Cl$_3$ | 3 | CH$_3$ | CH$_3$ | pyrazol-1-yl | m.p. 111° C |
| 18 | 1,2,3,4,5-Cl$_5$ | 5 | CH$_3$ | CH$_3$ | pyrazol-1-yl | m.p. 156° C |
| 19 | — | 0 | C$_2$H$_5$ | C$_2$H$_5$ | pyrazol-1-yl | $n_D^{20}$ 1.5689 |
| 20 | 3-CF$_3$ | 1 | CH$_3$ | CH$_3$ | pyrazol-1-yl | Hydrochloride $n_D^{20}$ 1.5086 |
| 21 | 4-Cl | 1 | CH$_3$ | CH$_3$ | pyrazol-1-yl | m.p. 110° C |
| 22 | 3-CF$_3$ | 1 | CH$_3$ | CH$_3$ | imidazol-1-yl | $n_D^{20}$ 1.5351 |

Table 1-continued (I)

$$\underset{(R^1)_n}{\phantom{xx}}\text{Ar}-N=C-Az \atop \underset{R^2\phantom{xx}R^3}{N}$$

| Ex. No. | R[1] | n | R[2] | R[3] | Az | Physical characteristics |
|---|---|---|---|---|---|---|
| 23 | 3,4-Cl$_2$ | 2 | CH$_3$ | CH$_3$ | imidazolyl | m.p. 98° C |
| 24 | 2,5-Cl$_2$ | 2 | CH$_3$ | CH$_3$ | imidazolyl | m.p. 110° C |
| 25 | 2,4-Cl$_2$ | 2 | CH$_3$ | CH$_3$ | imidazolyl | m.p. 67° C |
| 26 | 2,6-Cl$_2$ | 2 | CH$_3$ | CH$_3$ | imidazolyl | m.p. 106° C |
| 27 | 4-CH$_3$, 3-Cl | 2 | CH$_3$ | CH$_3$ | imidazolyl | m.p. 94° C |
| 28 | 4-OCH$_3$, 3-Cl | 2 | CH$_3$ | CH$_3$ | imidazolyl | m.p. 120° C |
| 29 | 2-CH$_3$, 4-Cl | 2 | CH$_3$ | CH$_3$ | imidazolyl | m.p. 118° C |
| 30 | 2-CF$_3$, 4-Cl | 2 | CH$_3$ | CH$_3$ | imidazolyl | m.p. 100° C |
| 31 | 2,4,6-Cl$_3$ | 3 | CH$_3$ | CH$_3$ | imidazolyl | m.p. 128° C |
| 32 | 1,2,3,4,5-Cl$_5$ | 5 | CH$_3$ | CH$_3$ | imidazolyl | m.p. 176° C |
| 33 | 3,5-Cl$_2$ | 2 | CH$_3$ | CH$_3$ | imidazolyl | m.p. 80° C |
| 34 | — | 0 | C$_2$H$_5$ | C$_2$H$_5$ | imidazolyl | $n_D^{20}$ 1.5723 |
| 35 | — | 0 | CH$_3$ | CH$_3$ | 1,2,4-triazolyl | m.p. 94° C |

Table 1-continued

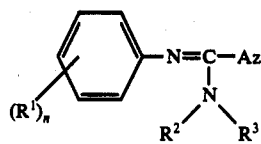
(I)

| Ex. No. | R¹ | n | R² | R³ | Az | Physical characteristics |
|---|---|---|---|---|---|---|
| 36 | 4-Cl | 1 | CH₃ | CH₃ | triazole | m.p. 117° C |
| 37 | 3-CF₃ | 1 | CH₃ | CH₃ | triazole | m.p. 120° C |
| 38 | 3,4-Cl₂ | 2 | CH₃ | CH₃ | triazole | m.p. 92° C |
| 39 | 2,6-Cl₂ | 2 | CH₃ | CH₃ | triazole | m.p. 132° C |
| 40 | 3,5-Cl₂ | 2 | CH₃ | CH₃ | triazole | m.p. 100° C |
| 41 | 2,4-Cl₂ | 2 | CH₃ | CH₃ | triazole | m.p. 98° C |
| 42 | 4-Cl, 2-CH₃ | 2 | CH₃ | CH₃ | triazole | m.p. 31° C |
| 43 | 4-Cl, 2-CF₃ | 2 | CH₃ | CH₃ | triazole | m.p. 90° C |
| 44 | 3-Cl, 4-OCH₃ | 2 | CH₃ | CH₃ | triazole | m.p. 89° C |
| 45 | 3-Cl, 4-CH₂ | 2 | CH₃ | CH₃ | triazole | m.p. 120° C |
| 46 | — | 0 | C₂H₅ | C₂H₅ | triazole | m.p. 71° C |
| 47 | — | 0 | CH₃ | CH₃ | 2-methylimidazole | m.p. 93° C |
| 48 | 3-Cl, 4-CH₃ | 2 | CH₃ | CH₃ | 2-methylimidazole | $n_D^{20}$ 1.5882 |

Table 1-continued (I)

structure: (R¹)ₙ–C₆H₄–N=C(Az)–N(R²)(R³)

| Ex. No. | R¹ | n | R² | R³ | Az | Physical characteristics |
|---|---|---|---|---|---|---|
| 49 | 3-Cl, 4-OCH₃ | 2 | CH₃ | CH₃ | 1-methyl-2-methylimidazol-2-yl | $n_D^{20}$ 1.5901 |
| 50 | 3,4-Cl₂ | 2 | CH₃ | CH₃ | 1-methyl-2-methylimidazol-2-yl | $n_D^{20}$ 1.6042 |
| 51 | 2,6-Cl₂ | 2 | CH₃ | CH₃ | 1-methyl-2-methylimidazol-2-yl | m.p. 109° C |
| 52 | 4-Cl | 1 | CH₃ | CH₃ | 1-methyl-2-methylimidazol-2-yl | m.p. 100° C |
| 53 | 2-CF₃, 4-Cl | 2 | CH₃ | CH₃ | 1-methyl-2-methylimidazol-2-yl | m.p. 63° C |
| 54 | 2,4,6-Cl₃ | 3 | CH₃ | CH₃ | 1-methyl-2-methylimidazol-2-yl | m.p. 103° C |
| 55 | 3,4-Cl₂ | 2 | CH₃ | CH₃ | 1-methyl-2-ethylimidazol-2-yl | $n_D^{20}$ 1.5959 |
| 56 | 2,6-Cl₂ | 2 | CH₃ | CH₃ | 1-methyl-2-ethylimidazol-2-yl | m.p. 64° C |
| 57 | 2-CF₃, 4-Cl | 2 | CH₃ | CH₃ | 1-methyl-2-ethylimidazol-2-yl | m.p. 86° C |
| 58 | — | 0 | CH₃ | CH₃ | 1-methyl-2-ethylimidazol-2-yl | $n_D^{20}$ 1.5736 |
| 59 | 4-Cl | 1 | CH₃ | CH₃ | 1-methyl-2-ethylimidazol-2-yl | $n_D^{20}$ 1.5842 |
| 60 | — | 0 | CH₃ | CH₃ | 1-methyl-2-propylimidazol-2-yl | $n_D^{20}$ 1.5380 |
| 61 | 4-Cl | 1 | CH₃ | CH₃ | 1-methyl-2-propylimidazol-2-yl | $n_D^{20}$ 1.5961 |

Table 1-continued (I)

Structure: aryl-N=C(Az)-N(R²)(R³), with (R¹)ₙ on phenyl ring

| Ex. No. | R¹ | n | R² | R³ | Az | Physical characteristics |
|---|---|---|---|---|---|---|
| 62 | 3,4-Cl₂ | 2 | CH₃ | CH₃ | 2-C₃H₇-imidazol-1-yl | $n_D^{20}$ 1.5866 |
| 63 | 2-CF₃, 4-Cl | 2 | CH₃ | CH₃ | 2-C₃H₇-imidazol-1-yl | m.p. 45° C |
| 64 | 2,6-Cl₂ | 2 | CH₃ | CH₃ | 2-C₃H₇-imidazol-1-yl | $n_D^{20}$ 1.5749 |
| 65 | — | 0 | CH₃ | CH₃ | 2-CH(CH₃)₂-imidazol-1-yl | m.p. 25° C |
| 66 | 4-Cl | 1 | CH₃ | CH₃ | 2-CH(CH₃)₂-imidazol-1-yl | m.p. 104° C |
| 67 | 2,6-Cl₂ | 2 | CH₃ | CH₃ | 2-CH(CH₃)₂-imidazol-1-yl | m.p. 140° C |
| 68 | 2-CF₃, 4-Cl | 2 | CH₃ | CH₃ | 2-CH(CH₃)₂-imidazol-1-yl | m.p. 113° C |
| 69 | 3-Cl, 4-CH₃ | 2 | CH₃ | CH₃ | 2-CH(CH₃)₂-imidazol-1-yl | m.p. 70° C |
| 70 | — | 0 | CH₃ | CH₃ | 4-CH₃-imidazol-1-yl | $n_D^{20}$ 1.5814 |
| 71 | 2,6-Cl₂ | 2 | CH₃ | CH₃ | 4-CH₃-imidazol-1-yl | m.p. 25° C |
| 72 | 2-CF₃, 4-Cl | 2 | CH₃ | CH₃ | 4-CH₃-imidazol-1-yl | $n_D^{20}$ 1.7087 |
| 73 | 2,6-Cl₂ | 2 | CH₃ | CH₃ | 4-NO₂-imidazol-1-yl | m.p. 110° C |
| 74 | 2-CF₃, 4-Cl | 2 | CH₃ | CH₃ | 4-NO₂-imidazol-1-yl | m.p. 120° C |

Table 1-continued (I)

| Ex. No. | R¹ | n | R² | R³ | Az | Physical characteristics |
|---|---|---|---|---|---|---|
| 75 | — | 0 | CH₃ | CH₃ | 4-CH₃, 2-CH₃ imidazolyl (N-Me) | $n_D^{20}$ 1.5892 |
| 76 | 4-Cl | 1 | CH₃ | CH₃ | 4-CH₃, 2-CH₃ imidazolyl (N-Me) | $n_D^{20}$ 1.5864 |
| 77 | 2,6-Cl₂ | 2 | CH₃ | CH₃ | 4-CH₃, 2-CH₃ imidazolyl (N-Me) | m.p. 25° C |
| 78 | 2-CF₃, 4-Cl | 2 | CH₃ | CH₃ | 4-CH₃, 2-CH₃ imidazolyl (N-Me) | $n_D^{20}$ 1.5449 |
| 79 | 2,6-Cl₂ | 2 | CH₃ | CH₃ | 4-CH₃, 5-NO₂ imidazolyl (N-Me) | m.p. 146° C |
| 80 | 2-CF₃, 4-Cl | 2 | CH₃ | CH₃ | 4-CH₃, 5-NO₂ imidazolyl (N-Me) | m.p. 112° C |
| 81 | 2,6-Cl₂ | 2 | CH₃ | CH₃ | 5-NO₂, 2-CH₃ imidazolyl (N-Me) | m.p. 140° C |
| 82 | 2-CF₃, 4-Cl | 2 | CH₃ | CH₃ | 5-NO₂, 2-CH₃ imidazolyl (N-Me) | m.p. 132° C |
| 83 | 3-CF₃, 4-Cl | 2 | CH₃ | CH₃ | imidazolyl | m.p. 89° C |
| 84 | 2-Cl | 1 | CH₃ | CH₃ | imidazolyl | m.p. 106° C |
| 85 | 3-Cl | 1 | CH₃ | CH₃ | imidazolyl | m.p. 88° C |
| 86 | — | 0 | H | C₂H₅ | imidazolyl | m.p. 114° C |

Table 1-continued
$$\text{(I)}$$
| Ex. No. | R¹ | n | R² | R³ | Az | Physical characteristics |
|---|---|---|---|---|---|---|
| 87 | — | 0 |  | |  | m.p. 114° C |
| 88 | — | 0 |  | |  | m.p. 140° C |
| 89 | 3-Cl | 1 | CH₃ | CH₃ |  | m.p. 58° C |
| 90 | — | 0 | CH₃ | CH₃ |  | m.p. 114° C |
| 91 | 4-Cl | 1 | CH₃ | CH₃ |  | m.p. 126° C |
| 92 | 3,4-Cl₂ | 2 | CH₃ | CH₃ | 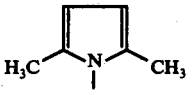 | m.p. 93° C |
| 93 | — | 0 | CH₃ | CH₃ | 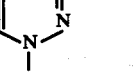 | m.p. 34° C |
| 94 | — | 0 | CH₃ | CH₃ | 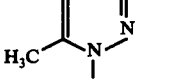 | $n_D^{20}$ 1.5836 |
| 95 | — | 0 | CH₃ | CH₃ | 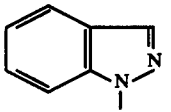 | $n_D^{20}$ 1.5750 |
| 96 | — | 0 | CH₃ | CH₃ |  | m.p. 132° C |
| 97 | — | 0 | CH₃ | CH₃ |  | m.p. 166° C |
| 98 | — | 0 | CH₃ | CH₃ | O₂N—(imidazole with 2-CH₃) | m.p. 92° C |

Table 1-continued (I)

| Ex. No. | R¹ | n | R² | R³ | Az | Physical characteristics |
|---|---|---|---|---|---|---|
| 99 | — | 0 | CH₃ | CH₃ | O₂N, H₃C-imidazole | m.p. 124° C |
| 100 | — | 0 | CH₃ | CH₃ | Cl,Cl-imidazole | m.p. 117° C |
| 101 | — | 0 | CH₃ | CH₃ | benzimidazole | m.p. 130° C |
| 102 | 3-Cl, 4-CF₃ | 2 | CH₃ | CH₃ | imidazole | $n_D^{20}$ 1.5510 |
| 103 | — | 0 | CH₃ | cyclohexyl | imidazole | m.p. 94° C |
| 104 | 3,4-Cl₂ | 2 | CH₃ | OCH₃ | imidazole | b.p. 150° C/0.05 mm Hg |
| 105 | 4-Cl | 1 | CH₃ | C₄H₉ | imidazole | $n_D^{21}$ 1,5760 |
| 106 | 3-Cl,4-OCH₃ | 2 | CH₃ | C₄H₉ | imidazole | b.p. 180° C/0.02 mmHg, $n_D^{20}$ 1.5721 |
| 107 | 3-Cl,4-SCH₃ | 2 | CH₃ | C₄H₉ | imidazole | b.p. 160 – 180° C/0.1 mmHg, $n_D^{20}$ 1.5700 |
| 108 | — | 0 | —CH₂—CH₂— | | imidazole | m.p. <25° C |
| 109 | 4-OC₂H₅ | 1 | CH₃ | CH₃ | imidazole | m.p. 122° C |
| 110 | 4-O-C₆H₄-Cl | 1 | CH₃ | CH₃ | imidazole | m.p. 94° C |

Table 1-continued (I)

$$\text{(R}^1\text{)}_n\text{—C}_6\text{H}_4\text{—N}=\text{C(Az)—N(R}^2\text{)(R}^3\text{)}$$

| Ex. No. | $R^1$ | n | $R^2$ | $R^3$ | Az | Physical characteristics |
|---|---|---|---|---|---|---|
| 111 | 4-SCClF$_2$ | 1 | CH$_3$ | CH$_3$ | pyrazol-1-yl | m.p. 74° C |
| 112 | 4-F | 1 | CH$_3$ | CH$_3$ | pyrazol-1-yl | m.p. 80° C |
| 113 | 3-F | 1 | CH$_3$ | CH$_3$ | pyrazol-1-yl | $n_D^{20}$ 1.5716 |
| 114 | 2-F | 1 | CH$_3$ | CH$_3$ | pyrazol-1-yl | m.p. 72° C |
| 115 | 4-Br | 1 | CH$_3$ | CH$_3$ | pyrazol-1-yl | m.p. 82° C |
| 116 | 4-CH$_3$ | 1 | CH$_3$ | CH$_3$ | pyrazol-1-yl | m.p. 85° C |
| 117 | 3-CH$_3$ | 1 | CH$_3$ | CH$_3$ | pyrazol-1-yl | b.p. 110° C/0.01 mm Hg |
| 118 | 2-CH$_3$ | 1 | CH$_3$ | CH$_3$ | pyrazol-1-yl | b.p. 115°C/0.1 mm Hg |
| 119 | 4-Cl | 1 | H | CH$_3$ | pyrazol-1-yl | b.p. 130° C/0.01 mm Hg |
| 120 | 3,4-Cl$_2$ | 2 | H | CH$_3$ | pyrazol-1-yl | m.p. 78° C |
| 121 | 3-Cl, 4-CF$_3$O | 2 | CH$_3$ | CH$_3$ | imidazol-1-yl | b.p. 160° C/0.01 mm Hg |
| 122 | 4-Cl | 1 | CH$_3$ | CH$_3$ | 4-nitroimidazol-1-yl | m.p. 116° C |
| 123 | 4-CF$_3$ | 1 | CH$_3$ | CH$_3$ | imidazol-1-yl | m.p. <25° C |
| 124 | 3-Cl, | | | | | |

Table 1-continued $$\underset{(R^1)_n}{\text{(structure)}} \quad N=C-Az \quad | \quad N \quad R^2 \quad R^3$$ (I)

| Ex. No. | R¹ | n | R² | R³ | Az | Physical characteristics |
|---|---|---|---|---|---|---|
| | 4-ClF₂CS | 2 | CH₃ | CH₃ | imidazolyl | m.p. 74° C |
| 125 | 4-F | 1 | CH₃ | CH₃ | imidazolyl | m.p. 70° C |
| 126 | 3-F | 1 | CH₃ | CH₃ | imidazolyl | m.p. 89° C |
| 127 | 4-Br | 1 | CH₃ | CH₃ | imidazolyl | m.p. 118° C |
| 128 | 3-F | 1 | CH₃ | CH₃ | imidazolyl | m.p. 65° C |
| 129 | 4-CH₃ | 1 | CH₃ | CH₃ | imidazolyl | m.p. 74° C |
| 130 | 3-CH₃ | 1 | CH₃ | CH₃ | imidazolyl | b.p. 135° C/0.01 mm Hg |
| 131 | 2-CH₃ | 1 | CH₃ | CH₃ | imidazolyl | m.p. 68° C |
| 132 | 3-CF₃ | 1 | CH₃ | CH₃ | triazolyl | m.p. 120° C |
| 133 | 4-F | 1 | CH₃ | CH₃ | triazolyl | m.p. 77° C |
| 134 | 4-Br | 1 | CH₃ | CH₃ | triazolyl | m.p. 108° C |
| 135 | 2-F | 1 | CH₃ | CH₃ | triazolyl | m.p. 100° C |
| 136 | 2-CH₃ | 1 | CH₃ | CH₃ | triazolyl | m.p. 102° C |

Table 1-continued (I)

| Ex. No. | R¹ | n | R² | R³ | Az | Physical characteristics |
|---|---|---|---|---|---|---|
| 137 | 3-CH₃ | 1 | CH₃ | CH₃ | 1,2,4-triazol-1-yl | m.p. 52° C |
| 138 | 4-Br | 1 | CH₃ | CH₃ | 1,2,4-triazol-1-yl | m.p. 172° C |
| 139 | 2-F | 1 | CH₃ | CH₃ | 1,2,4-triazol-1-yl | m.p. 150° C |
| 140 | 4-F | 1 | CH₃ | CH₃ | 1,2,3-triazol-1-yl | m.p. 130° C |
| 141 | — | 0 | CH₃ | C₄H₉ | 1,2,4-triazol-1-yl | b.p. 102–110° C/0.2 mm Hg $n_D^{20}$ 1.5498 |
| 142 | — | 0 | CH₃ | C₄H₉ | imidazol-1-yl | b.p. 98–100° C/0.2 mm Hg $n_D^{20}$ 1.5700 |
| 143 | 3-Cl 4-CH₃O | 2 | CH₃ | C₄H₉ | 1,2,4-triazol-1-yl | m.p. 72° C |
| 144 | 3-Cl 4-CH₃O | 2 | CH₃ | C₄H₉ | pyrazol-1-yl | b.p. 175–180° C/0.2 mm Hg $n_D^{20}$ 1.5775 |
| 145 | 3,4-Cl₂ | 2 | H | C₂H₅ | pyrazol-1-yl | m.p. 80° C |
| 146 | 3-Cl 4-CH₃S | 2 | CH₃ | C₄H₉ | pyrazol-1-yl | b.p. 182° C/0.1 mm Hg $n_D^{20}$ 1.5849 |
| 147 | 3-Cl 4-CH₃S | 2 | CH₃ | C₄H₉ | 1,2,4-triazol-1-yl | b.p. 185° C/0.1 mm Hg $n_D^{20}$ 1.5742 |
| 148 | — | 0 | (pyrrolidine) | | imidazol-1-yl | Hydrochloride, m.p. 180° C |
| 149 | 4-Cl | 1 | CH₃ | CH₃ | imidazol-1-yl | Hydrochloride, m.p. 100° C |
| 150 | 4-Cl | 1 | CH₃ | CH₃ | pyrazol-1-yl | Hydrochloride, m.p. 110° C |

Table 1-continued

| Ex. No. | R¹ | n | R² | R³ | Az | Physical characteristics |
|---|---|---|---|---|---|---|
| 151 | 2-CF₃, 4-Cl | 2 | CH₃ | CH₃ | imidazole-CH(CH₃)₂ | Hydrochloride, m.p. 140° C |
| 152 | — | 0 | \-tetrahydropyran- | | imidazole | Hydrochloride, m.p. 45° C |
| 153 | — | 0 | CH₃ | CH₃ | benzimidazole | Hydrochloride, m.p. 130° C |
| 154 | 3-CH₃ | | CH₃ | CH₃ | imidazole | Hydrochloride, m.p. < 20° C |
| 155 | 4-Cl | 1 | CH₃ | CH₃ | 1,2,4-triazole | Hydrochloride, m.p. 170° C |
| 156 | 3-CF₃ | 1 | CH₃ | CH₃ | 1,2,4-triazole | Hydrochloride, m.p. 80° C |
| 157 | — | 0 | CH₃ | CH₃ | 1,2,4-triazole | Hydrochloride, m.p. 150° C |
| 158 | 4-Cl | 1 | CH₃ | CH₃ | pyrazole | Hydrochloride, m.p. 165° C |
| 159 | — | 0 | CH₃ | CH₃ | indazole | Hydrochloride, m.p. 110° C |
| 160 | — | 0 | CH₃ | CH₃ | pyrazole | Hydrochloride, m.p. 140° C |
| 161 | 3-CH₃ | 1 | CH₃ | CH₃ | pyrazole | Hydrochloride, m.p. < 20° C |
| 162 | — | 0 | CH₃ | CH₃ | imidazole | Hydrochloride, m.p. 100° C |
| 163 | — | 0 | CH₃ | cyclohexyl-H | imidazole | Hydrochloride, m.p. 120° C |
| 164 | 2-Cl | 1 | CH₃ | CH₃ | imidazole | Hydrochloride, m.p. 60° C |

The active compounds according to the invention possess excellent herbicidal properties and can therefore be used for combating weeds.

Weeds in the broadest sense are plants which grow in places where they are not desired. As weeds there may be mentioned: dicotyledons, such as mustard (Sinapis), cress (Lepidum), cleavers (Galium), chickweed (Stellaria), camomile (Matricaria), gallant soldier (Galinsoga), goosefoot (Chenopodium), annual nettle (Urtica) and groundsel (Senecio) and monocotyledons, such as timothy (Phleum), bluegrass (Poa), fescue (Festuca), goosegrass (Eleusine), foxtail (Setaria), rye grass (Lolium) and barnyard grass (Echinochloa).

The active compounds according to the invention greatly influence plant growth, but in different ways, so that they can be used as selective herbicides. They show particular advantages as selective herbicides in cultures of cotton, corn and cereals. In higher concentrations, they can also be employed as total weedkillers (approximately 10 – 20 kg/ha).

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds.

The formulations, in general, contain from 0.1 to 95 percent by weight of active compound, preferably from 0.5 to 90 percent by weight.

The active compounds can be used as such, in the form of their formulations or in the application forms prepared therefrom, such as ready-to-use solutions, emulsions, suspensions, powders, pastes and granules. They may be used in the customary manner, for example, by watering, spraying, atomizing, scattering or dusting.

They can be used either by the post-emergence process or by the pre-emergence process; they are preferably used after the emergence of the plants.

The amount of active compounds employed can vary within fairly wide ranges. It depends essentially on the nature of the desired effect. In general, the amounts used are from 0.1 to 25 kg/ha, preferably from 0.5 to 10 kg/ha.

The present invention also provides a herbicidal composition containing an active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides methods of securing crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The active compounds according to the invention also display a good acaricidal activity. In addition, the fungicidal action of some compounds of formula (I), especially against species of cereal mildew, Erysiphe and Puccinia, should be mentioned.

The herbicidal activity of the present compounds is illustrated in the following test Examples.

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was then diluted with water to the desired concentration.

Test plants, which had a height of 5–15 cm, were sprayed with the preparation of the active compound so that the amounts of active compound per unit area stated in the table were applied. Depending on the concentration of the spray liquor, the amount of water used was between 1,000 and 2,000 l/hectare. After three weeks, the degree of damage to the plants was determined and characterized by the values 0–5, which had the following meaning:

0 — no effect
1 — a few slightly burnt spots
2 — marked damage to leaves
3 — some leaves and parts of stalks partially dead
4 — plant partially destroyed
5 — plant completely dead The active compounds, the amounts applied and the results obtained can be seen from the following table:

Table A

Post-emergence test

| Active compound | Amount of active compound used, kg/ha | Echino-chloa | Cheno-podium | Sina-pis | Galin-soga | Stella-ria | Urti-ca | Matri-caria | Oats | Cot-ton | Wheat |
|---|---|---|---|---|---|---|---|---|---|---|---|
| Cl—C6H4—N=C(N(CH3)2)—imidazolyl (21) | 2<br>1 | 5<br>4 | 5<br>5 | 5<br>4 | 5<br>4 | 5<br>3 | 5<br>3 | 5<br>4 | 4<br>3 | 3<br>2 | 2<br>0 |
| Cl—C6H4—N=C(N(CH3)2)—pyrazolyl (2) | 2<br>1 | 5<br>5 | 5<br>4 | 5<br>5 | 5<br>5 | 5<br>5 | 5<br>5 | 5<br>5 | 4<br>4 | 1<br>0 | 4<br>3 |
| C6H5—N=C(N(CH3)2)—imidazolyl (3) | 2<br>1 | 5<br>4 | 5<br>4–5 | 5<br>5 | 5<br>5 | 5<br>4 | 5<br>5 | 5<br>4 | 4–5<br>4 | 2<br>1 | 2<br>1 |
| C6H5—N=C(N(CH3)2)—N(CH3)2 (known) | 2<br>1 | 3<br>2 | 2<br>0 | 2<br>0 | 0<br>0 | 0<br>0 | 0<br>0 | 0<br>0 | 2<br>0 | 0<br>0 | 2<br>1 |
| Cl—C6H4—N=C(N(CH3)2)—triazolyl (36) | 2<br>1 | 5<br>4 | 4<br>3 | 5<br>5 | 5<br>4 | 5<br>4 | 5<br>5 | 5<br>5 | 4<br>3 | 1<br>0 | 4<br>3 |

EXAMPLE B

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0–5, which had the following meaning:

0 — no effect
1 — slight damage or delay in growth
2 — marked damage or inhibition of growth
3 — heavy damage and only deficient development or only 50% emerged
4 — plants partially destroyed after germination or only 25% emerged
5 — plants completely dead or not emerged.

The active compounds, the amounts applied and the results obtained can be seen from the following table:

Table B

| Active compound | Amount of active compound used, kg/ha | Echino-chloa | Cheno-podium | Sina-pis | Loli-um | Stella-ria | Galin-soga | Matri-caria | Cot-ton | Wheat | Corn |
|---|---|---|---|---|---|---|---|---|---|---|---|
| Cl—C6H4—N=C(N(CH3)2)—imidazolyl (21) | 5<br>2.5 | 5<br>5 | 5<br>5 | 5<br>5 | 5<br>5 | 5<br>5 | 5<br>5 | 5<br>5 | 1<br>0 | 5<br>4 | 3<br>3 |

Table B-continued

| Active compound | Amount of active compound used, kg/ha | Pre-emergence test. | | | | | | | | | |
|---|---|---|---|---|---|---|---|---|---|---|---|
| | | Echino-chloa | Cheno-podium | Sina-pis | Loli-um | Stella-ria | Galin-soga | Matri-caria | Cot-ton | Wheat | Corn |
| 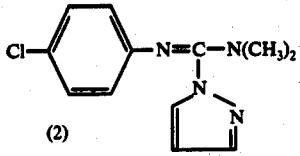 (2) | 5<br>2.5 | 5<br>5 | 5<br>5 | 5 | 5<br>5 | 5<br>5 | 5<br>5 | 5<br>5 | 3<br>2 | 4<br>3 | 4<br>3 |
| 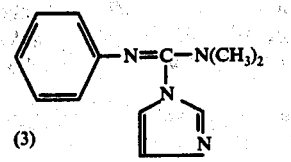 (3) | 5<br>2.5 | 5<br>5 | 5<br>5 | 5<br>5 | 5<br>5 | 5<br>5 | 5<br>5 | 5<br>5 | 1<br>0 | 4<br>4 | 2<br>0 |
| 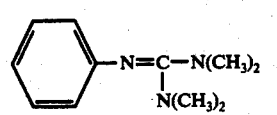 (known) | 5<br>2.5 | 2<br>1 | 2<br>2 | 4<br>3-4 | 0<br>0 | 2<br>2 | 4<br>3 | 4-5<br>3 | 2<br>0 | 3<br>3 | 1<br>0 |
| 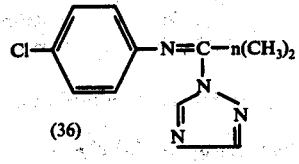 (36) | 5<br>2.5 | 5<br>5 | 5<br>5 | 5<br>5 | 5<br>5 | 5<br>5 | 5<br>5 | 5<br>5 | 0<br>0 | 2<br>1 | 1<br>0 |
| 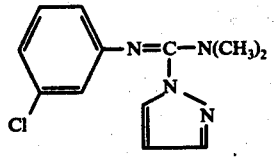 (89) | 5<br>2.5 | 5<br>5 | 5<br>5 | 5<br>5 | 5<br>4 | 5<br>5 | 5<br>5 | 5<br>5 | 0<br>0 | 4<br>3 | 2<br>1 |
| 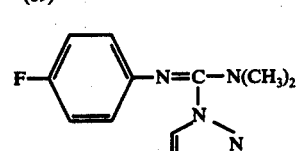 (112) | 5<br>2.5 | 5<br>5 | 5<br>5 | 5<br>5 | 5<br>5 | 5<br>5 | 5<br>5 | 5<br>5 | 2<br>1 | 4<br>3 | 4<br>4 |

It will be understood that the specification and examples are illustrative but not limitative of the present invention and that other embodiments within the spirit and scope of the invention will suggest themselves to those skilled in the art.

What is claimed is:

1. Azolylamidine compound of the formula

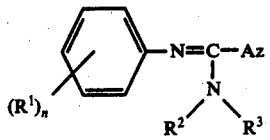

(I)

wherein
n is an integer from 0 to 5, inclusive, $R^1$ is individually selected from halogen, alkyl, alkoxy, alkylthio, haloalkoxy, haloalkylthio, halophenoxy and haloalkyl and contains not more than 6 carbon atoms;
$R^2$ and $R^3$ are independently selected from hydrogen, alkyl, alkoxyalkyl, cycloalkyl, alkoxy and alkoxycarbonylalkyl and contains not more than 7 carbon atoms;
$R^2$ and $R^3$, taken together, represent a lower alkylene bridge;
Az is pyrazol-1-yl.

2. Azolylamidine compound as claimed in claim 1 wherein n is 0.

3. Azolylamidine compound as claimed in claim 1 wherein n is 1.

4. Azolylamidine compound as claimed in claim 1 wherein n is 2.

5. Azolylamidine compound as claimed in claim 1 wherein n is 3.

6. Azolylamidine compound as claimed in claim 1 wherein n is 4 or 5.

7. Azolylamidine compound as claimed in claim 1 wherein $R^1$ is halogen.

8. Azolylamidine compound as claimed in claim 1 wherein $R^1$ is alkyl.

9. Azolylamidine compound as claimed in claim 1 wherein $R^1$ is alkoxy, alkylthio, haloalkoxy or haloalkylthio.

10. Azolylamidine compound as claimed in claim 1 wherein $R^1$ is halophenoxy.

11. Azolylamidine compound as claimed in claim 1 wherein $R^1$ is haloalkyl.

12. Azolylamidine compound as claimed in claim 1 wherein one of $R^2$ and $R^3$ is hydrogen.

13. Azolylamidine compound as claimed in claim 1 wherein one of $R^2$ and $R^3$ is alkyl.

14. Azolylamidine compound as claimed in claim 1 wherein one of $R^2$ and $R^3$ is alkoxyalkyl.

15. Azolylamidine compound as claimed in claim 1 wherein one of $R^2$ and $R^3$ is cycloalkyl.

16. Azolylamidine compound as claimed in claim 1 wherein one of $R^2$ and $R^3$ is alkoxy.

17. Azolylamidine compound as claimed in claim 1 wherein one of $R^2$ and $R^3$ is alkoxycarbonylalkyl.

18. Azolylamidine compound as claimed in claim 1 wherein $R^2$ and $R^3$ taken together are lower alkylene of up to 5 carbon atoms.

19. Azolylamidine compound as claimed in claim 1 designated N(4-chlorophenyl)-N',N'-dimethyl-pyrazolyl-(1)-amidine.

20. Herbicidal composition comprising herbicidally acceptable carrier and, in effective amounts, an azolylamidine compound as claimed in claim 1.

21. Method of combatting undesired vegetation, which method comprises applying to said vegetation or its habitat a herbicidally effective amount of an azolylamidine compound of the formula

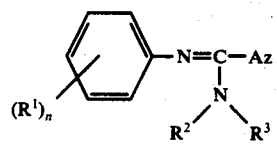

(I)

wherein
$n$ is an integer from 0 to 5, inclusive,
$R^1$ is individually selected from halogen, alkyl, alkoxy, alkylthio, haloalkoxy, haloalkylthio, halophenoxy and haloalkyl and contains not more than 6 carbon atoms;
$R^2$ and $R^3$ are independently selected from hydrogen, alkyl, alkoxyalkyl, cycloalkyl, alkoxy and alkoxycarbonylalkyl and contains not more than 7 carbon atoms;
$R^2$ and $R^3$, taken together, represent a lower alkylene bridge;
Az is pyrazol-1-yl.

22. Method as claimed in claim 21 wherein said compound is applied to weeds growing in a crop cultivation to selectively damage the weeds without substantial injury to the crops.

23. Method as claimed in claim 20 wherein said compound is selected from
N-(3-chlorophenyl)-N',N'-dimethyl-pyrazolyl-(1)-amidine.

* * * * *